(12) United States Patent
Hirthammer

(10) Patent No.: US 10,143,140 B2
(45) Date of Patent: Dec. 4, 2018

(54) CROP TRANSFER DEVICE AND CORRESPONDING METHOD

(71) Applicant: EXEL INDUSTRIES, Epernay (FR)

(72) Inventor: Daniel Hirthammer, Hirschling (DE)

(73) Assignee: EXEL INDUSTRIES, Epernay (FR)

(*) Notice: Subject to any disclaimer, the term of this patent is extended or adjusted under 35 U.S.C. 154(b) by 158 days.

(21) Appl. No.: 15/343,919

(22) Filed: Nov. 4, 2016

(65) Prior Publication Data

US 2017/0127617 A1 May 11, 2017

(30) Foreign Application Priority Data

Nov. 6, 2015 (EP) ..................................... 15306760

(51) Int. Cl.
| | |
|---|---|
| *A01D 90/10* | (2006.01) |
| *G01N 21/27* | (2006.01) |
| *A01D 33/10* | (2006.01) |
| *A01D 43/073* | (2006.01) |
| *A01D 51/00* | (2006.01) |
| *G01N 33/02* | (2006.01) |

(52) U.S. Cl.
CPC ............. *A01D 90/10* (2013.01); *A01D 33/10* (2013.01); *A01D 43/073* (2013.01); *A01D 51/005* (2013.01); *G01N 21/27* (2013.01); *G01N 33/025* (2013.01)

(58) Field of Classification Search
CPC ............................... A01D 90/10; G01N 21/27
USPC ............. 348/91; 56/10.2 R; 198/301; 141/83
See application file for complete search history.

(56) References Cited

U.S. PATENT DOCUMENTS

| | | | | |
|---|---|---|---|---|
| 6,943,824 B2* | 9/2005 | Alexia | ................. | A01D 43/073 348/120 |
| 8,234,047 B2* | 7/2012 | Madsen | ............... | A01D 43/073 56/10.2 R |
| 8,428,829 B2* | 4/2013 | Brunnert | ............. | A01D 43/087 56/10.2 F |
| 8,451,139 B2* | 5/2013 | Morselli | ............. | A01B 69/008 340/901 |

(Continued)

FOREIGN PATENT DOCUMENTS

| | | |
|---|---|---|
| EP | 2138027 A1 | 12/2009 |
| EP | 2873315 A1 | 5/2015 |

(Continued)

OTHER PUBLICATIONS

Extended European Search Report for EP Application 15306760.8 dated May 20, 2016.

*Primary Examiner* — Douglas A Hess
(74) *Attorney, Agent, or Firm* — Thompson Coburn LLP; Steven M. Ritchey

(57) ABSTRACT

Crop transfer device (4) for transferring crop to a receptacle, the device comprising a conveyor (8) for transferring the crop and the conveyor defining a conveyor plane (CP). The conveyor has a conveyor outlet (10) defining an outlet direction (OD) which is the direction of the crop falling from the conveyor at the conveyor outlet. The crop transfer device (4) comprises a scanning device (12) adapted to scan the surface of crop situated below the conveyor outlet and the crop transfer device (4) comprises a mounting device (14) by which the scanning device is mounted to the conveyor (8) with a translational mobility of the scanning device with respect to the conveyor along a path (20).

18 Claims, 4 Drawing Sheets

(56) References Cited

U.S. PATENT DOCUMENTS

| | | | |
|---|---|---|---|
| 8,682,540 B2* | 3/2014 | Missotten | A01D 43/087 701/50 |
| 8,868,304 B2* | 10/2014 | Bonefas | B65G 67/24 701/117 |
| 9,002,591 B2* | 4/2015 | Wang | A01D 41/1278 701/50 |
| 9,119,342 B2* | 9/2015 | Bonefas | A01D 34/001 |
| 9,313,951 B2* | 4/2016 | Herman | A01D 43/087 |
| 9,326,443 B2* | 5/2016 | Zametzer | A01D 41/127 |
| 9,326,444 B2* | 5/2016 | Bonefas | A01D 43/087 |
| 9,345,194 B2* | 5/2016 | Schroeder | A01D 41/127 |
| 9,392,746 B2* | 7/2016 | Darr | A01D 43/087 |
| 9,408,347 B2 | 8/2016 | Menke et al. | |
| 9,655,301 B2* | 5/2017 | Missotten | A01D 43/087 |

FOREIGN PATENT DOCUMENTS

| | | |
|---|---|---|
| GB | 2307893 A | 6/1997 |
| NL | 7709550 A | 3/1978 |
| WO | 2014/029824 A1 | 2/2014 |

\* cited by examiner

CROP TRANSFER DEVICE AND CORRESPONDING METHOD

CROSS-REFERENCE TO RELATED APPLICATIONS

The present application is a non-provisional application claiming the benefit of European Patent Application No. 15306760.8, filed Nov. 6, 2015, which is incorporated herein by reference in its entirety.

FIELD OF THE INVENTION

The present invention relates to a crop transfer device for transferring crop to a receptacle, the device comprising a conveyor for transferring the crop, the conveyor defining a conveyor plane (CP), and the conveyor having a conveyor outlet defining an outlet direction (OD) which is the direction of the crop falling from the conveyor at the conveyor outlet.

BACKGROUND OF INVENTION

It is known to convey crop, in particular crop from a root heap to a truck, using a transfer loader such as the Holmer Terra Felis 2. The transfer loader comprises a conveyor conveying the root crop into the receptacle of the truck. It is known to move the conveyor with respect to the receptacle manually in order to fill the receptacle uniformly.

SUMMARY OF INVENTION

The invention seeks to facilitate the loading operation for the operator and this with economical means.

The objective of the invention is achieved by a crop transfer device for transferring crop to a receptacle, the crop transfer device comprising:
a conveyor for transferring the crop, the conveyor defining a conveyor plane (CP), the conveyor having a conveyor outlet defining an outlet direction (OD) which is the direction of the crop falling from the conveyor at the conveyor outlet;
a scanning device adapted to scan the surface of crop situated below the conveyor outlet; and
a mounting device by which the scanning device is mounted to the conveyor with a translational mobility of the scanning device with respect to the conveyor along a path.

Various embodiments of the crop transfer device comprise one or more of the following features:
the mounting device comprises a mounting arm rotationally linked to the conveyor around a mounting axis of rotation (x-x) and wherein the scanning device is attached to the mounting arm at a distance to the mounting axis of rotation, in particular so that the path has an arc shape;
the scanning device is attached to the mounting arm at a distance to the mounting axis of rotation so that the path has an arc shape;
the scanning device is arranged above the conveyor plane with respect to the outlet direction;
the conveyor comprises an outlet wall and wherein the path of the scanning device is situated outside of the outlet wall, which is a side of the wall opposite the conveyor outlet;
the outlet wall extends perpendicular to the conveyor plane;
the path is situated completely on the outside of the outlet wall;
the scanning device comprises a scan head adapted to scan in a scan plane (SP);
the scan head comprises a 2D-Laserscanner;
the scan head is a rotational scan head having a rotational mobility around a scan axis (A-A);
the mounting device comprises drive means for driving the scanning device along the path;
the mounting device comprises drive means for driving the scanning device along the path and wherein the drive device comprises a linkage translating a unidirectional rotary motion of around more than 360° into an oscillating translation of the scanning device along the path;
the crop transfer device comprises control means adapted to generate a three-dimensional model of the crop heap surface and the receptacle based on the information generated by the scanning device;
the crop transfer device comprises control means adapted to generate a three-dimensional model of the crop heap surface or the receptacle based on the information generated by the scanning device; and
the crop transfer device is a device for transferring root crop.

The invention also refers to a method of transferring crop into a receptacle using a crop transfer device as defined above, the method comprising:
conveying crop via the conveyor;
discharging the conveyed crop through the conveyor outlet;
scanning the surface of a heap in the receptacle created by the discharged crop and/or the receptacle by the scanning device; and
moving the conveyor with respect to the receptacle as a function of the information generated by the scanning device.

DETAILED DESCRIPTION OF INVENTION

Figure 1:
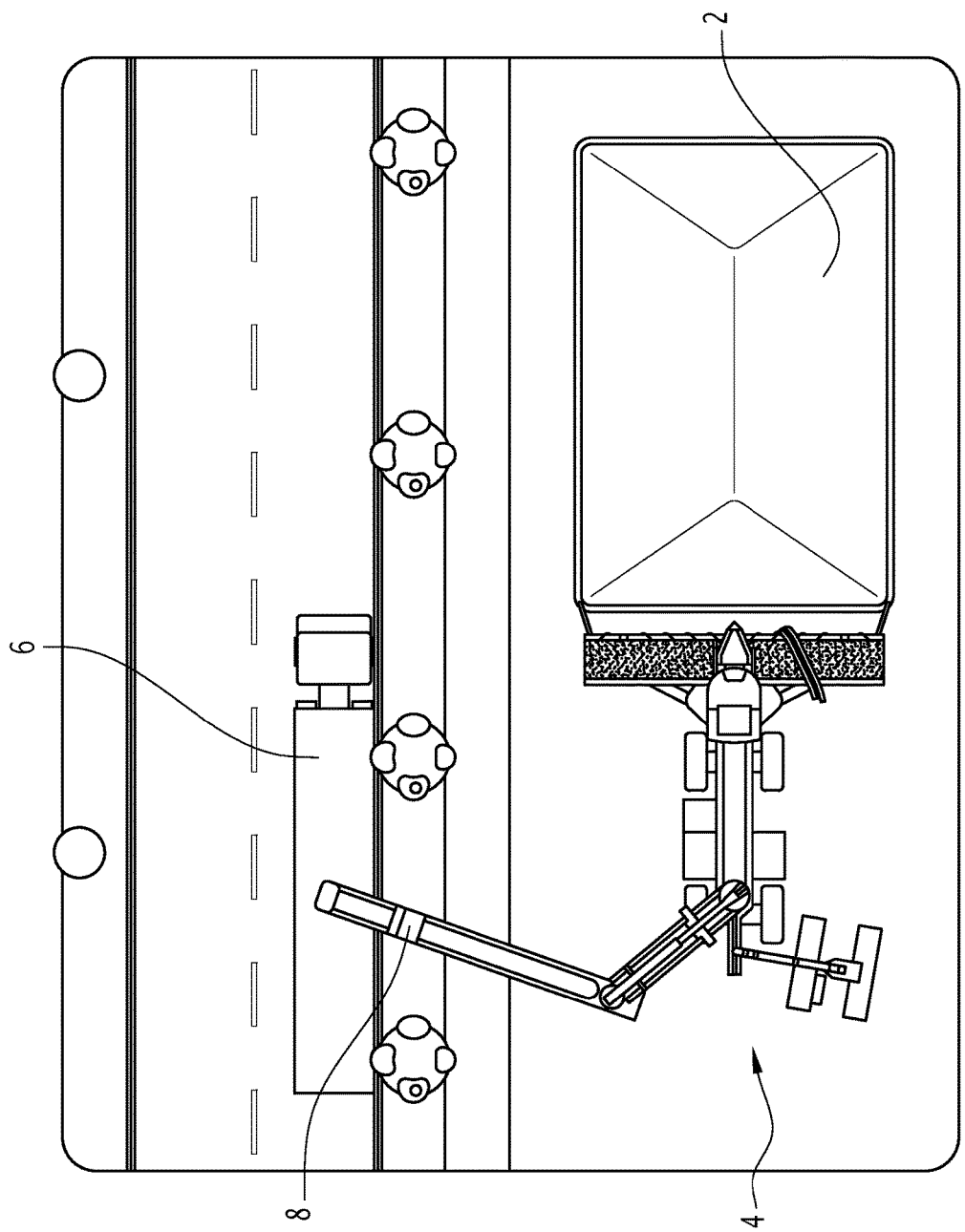
FIG. 1 is a schematic plane view of a crop transfer device according to the invention transferring crop to a transport vehicle.

The invention will be better understood in light of the following description, given only as an example and referring to the figures. FIG. 1 shows the situation of a crop transfer device according to the invention transferring root crop to a receptacle.

Crop 2 is arranged on a crop heap, for example at the lateral side of a field. The crop heap comprises for example root crop, such as sugar beets. A crop transfer device 4 is shown as well as a vehicle for transporting the crop. The vehicle comprises a receptacle 6 for the crop, such as a container. The vehicle may be a truck.

Figure 2:
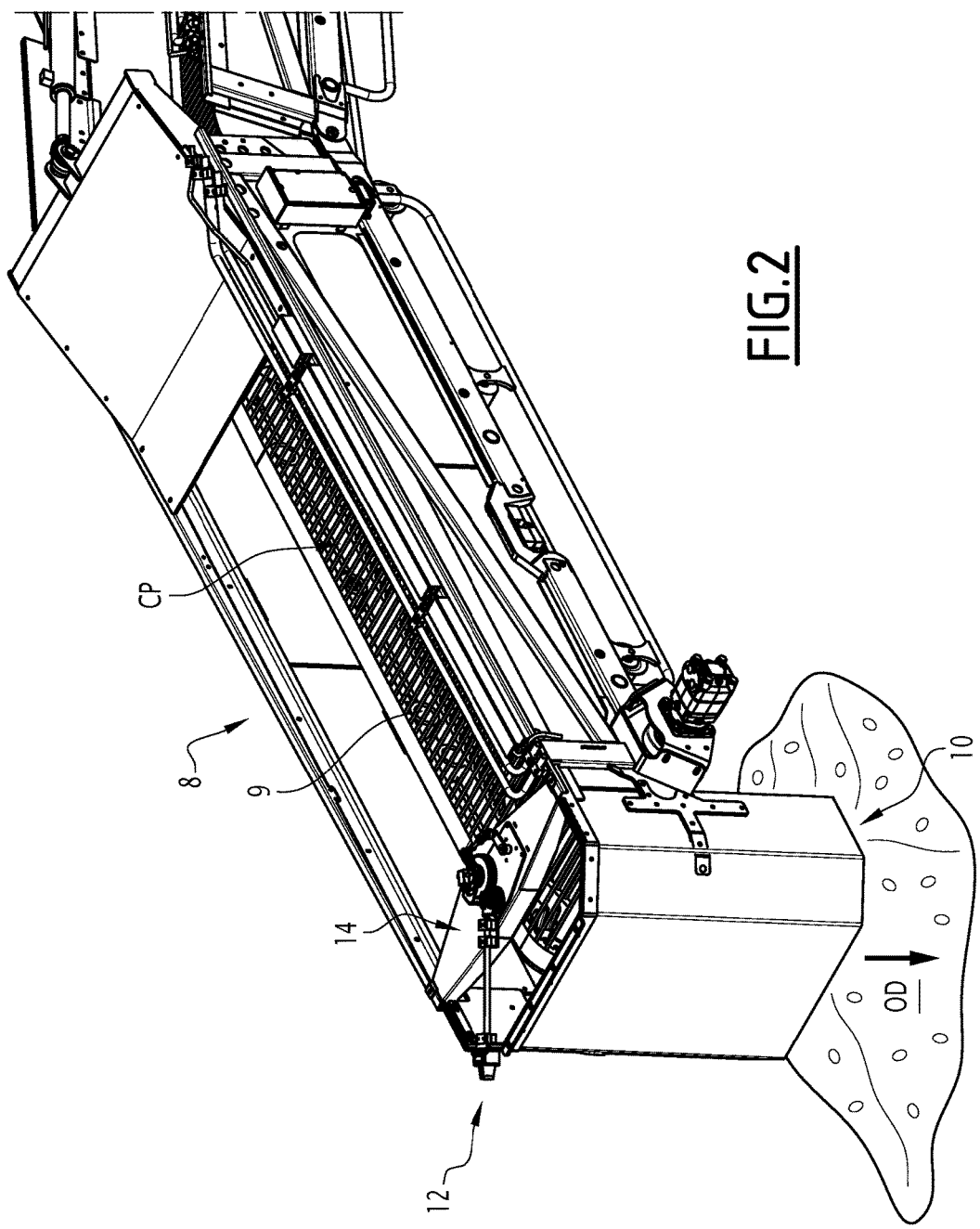
FIG. 2 is a perspective view of a portion of a conveyor for transferring the crop of the transfer loader of FIG. 1.
Figure 3:
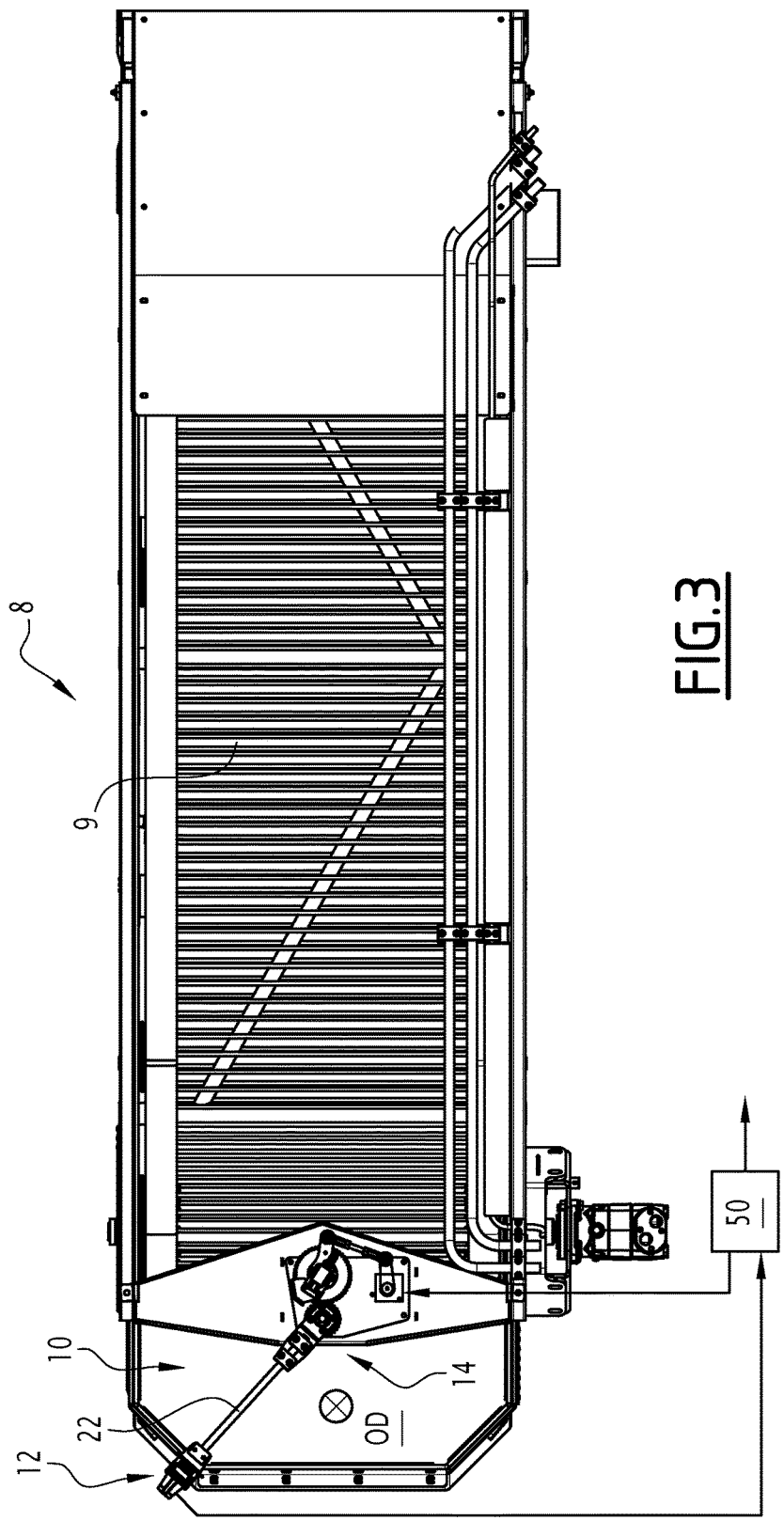
FIG. 3 is a plan view of the portion of the conveyor transfer device of FIG. 2.

The crop transfer device 4 is adapted for transferring the crop 2 of the crop heap to the receptacle 6 and comprises a conveyor 8 for transferring the crop. As can be seen on FIG. 2, the conveyor 8 defines a conveyor plane CP which is coplanar with the upper side of a conveyor belt 9. The conveyor plane CP is during use generally horizontal and parallel to the drawing plane of FIG. 3.

The conveyor 8 has a conveyor outlet 10 defining an outlet direction OD which is the direction of the crop 2 falling from the conveyor 8 at the conveyor outlet. The outlet direction OD is generally directed to the bottom of FIG. 2 and into the drawing plane FIG. 3.

Figure 4:
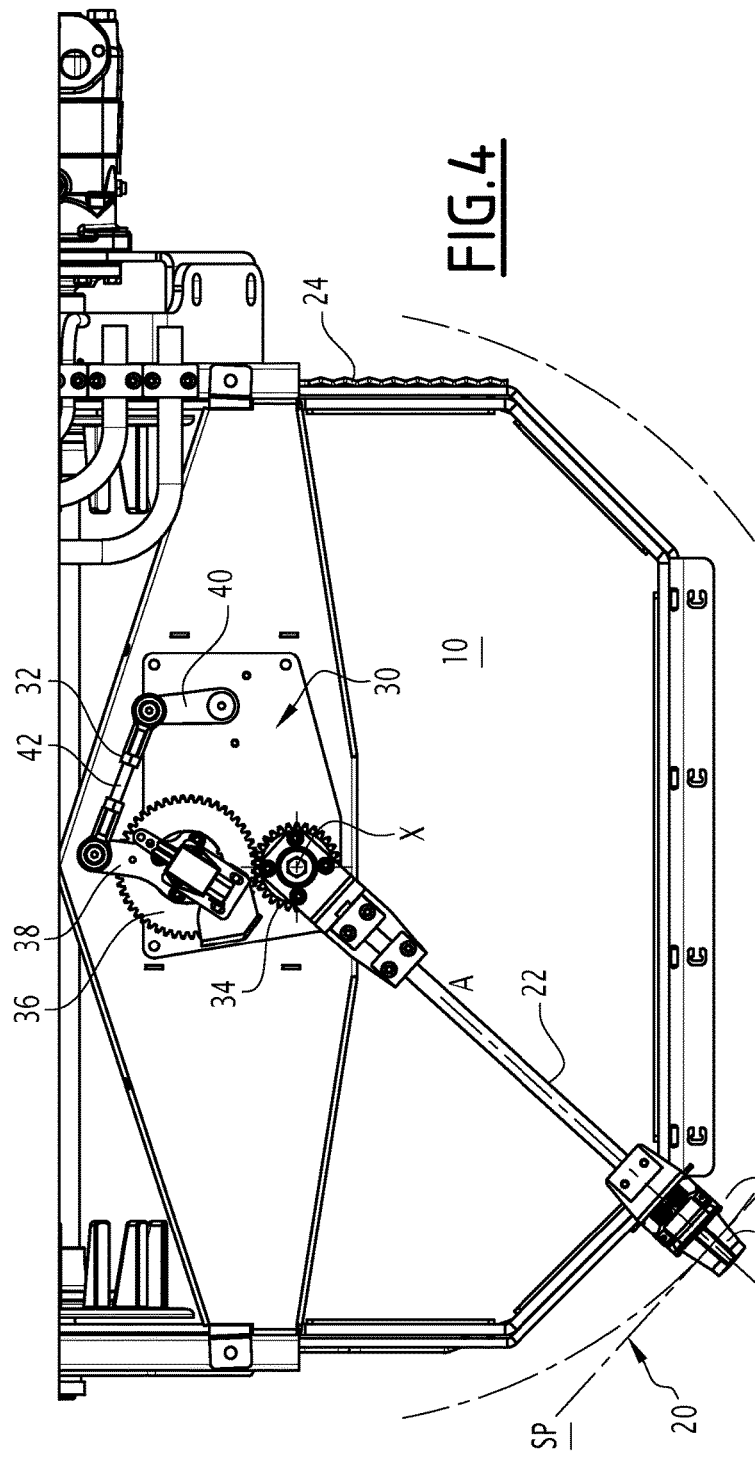
FIG. 4 is an enlarged view of the end portion of the conveyor.
Figure 5:
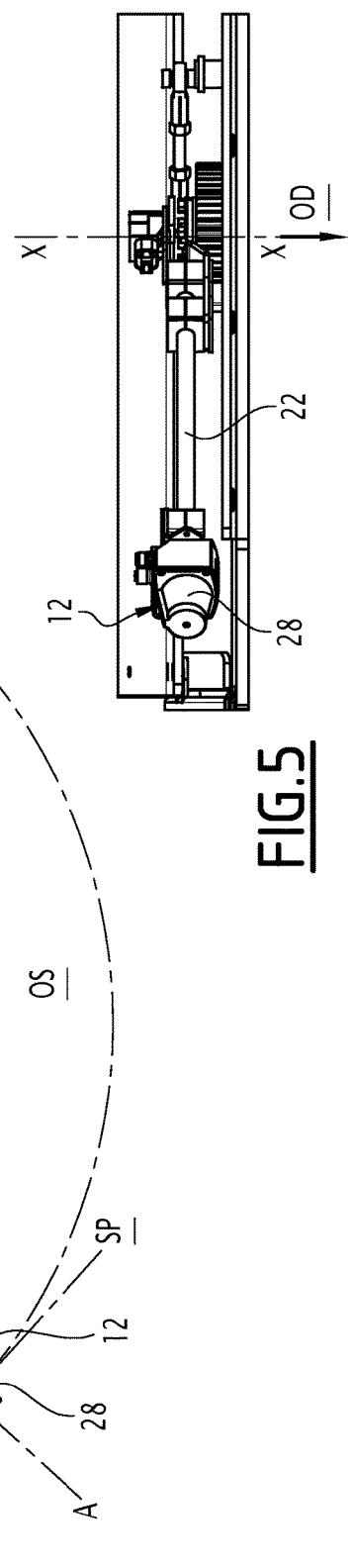
FIG. 5 is a front view of a portion of the crop transfer device.

The crop transfer device 4 comprises a scanning device 12 adapted to scan the surface of crop situated below the conveyor outlet 10 and/or the surface of the receptacle 6. The crop transfer device 4 comprises a mounting device 14 by which the scanning device 12 is mounted to the conveyor 8. The mounting device 14 maintains the scanning device 12 with respect to the conveyor 8 with a translational mobility of the scanning device 12 with respect to the conveyor along a path 20 (see FIG. 4). The mounting device 14 comprises a mounting arm 22 rotationally linked to the conveyor 8 around a mounting axis of rotation X-X and the scanning device 12 is attached to the mounting arm 22 at a distance to the mounting axis of rotation X-X. The path 20 has therefore an arc shape and in particular a circular arc shape. The path 20 extends at least over a region of 90° around the mounting axis of rotation X-X and preferably over at least 120° or 180° around the axis X-X.

The scanning device 12 is arranged above the conveyor plane CP with respect to the outlet direction, the mounting arm 22 does therefore not hinder the chute of the crop 2 from the conveyor outlet 10.

The conveyor outlet 10 comprises an outlet wall 24. The outlet wall 24 defines a channel guiding the crop 2 downwards. The outlet wall 24 extends preferably perpendicular to the conveyor plane CP and comprises a front wall and two lateral walls. The front and lateral walls are preferably perpendicular to the conveyor plane CP. The outlet wall 24 defines also an outside OS which is a side of the outlet wall opposite the conveyor outlet.

The path 20 of the scanning device is situated outside of the outlet wall 24. Preferably the path 22 is situated completely on the outside of the outlet wall 24. In other terms, the scanning device 12 in each position along the path 20 has a projection onto the conveyor plane CP that is located completely outside the projection of the outlet wall 24 on the conveyor plane. In this manner, the crop 2 falling onto the crop already in the receptacle do not enter the scan area. Also, the wall 24 does not generate scan artifacts.

The scanning device 12 comprises a scan head 28 adapted to scan in a scan plane SP. The scan plane SP extends perpendicularly to the conveyor plane CP and extends in particular exclusively perpendicular to the conveyor plane CP. In other words, the scan plane SP is fixed with respect to the mounting arm 22 and cannot be adjusted. The scan plane SP also extends parallel to the axis of rotation X-X in each of the positions of the scanning device along the path 20. The scan head 28 scans preferably exclusively in the scan plane SP. This means that the scan head 28 is fixed with respect to the mounting arm 22. In particular, the scan head 28 comprises a 2D-laser scanner. The scan head 28 is a rotating scan head having a rotational mobility around a scan axis A-A. The scan axis A-A is perpendicular to the scan plane SP and/or parallel to the conveyor plane CP.

The mounting device 14 comprises also drive means 30 for driving the scanning device 12 along the path 20.

The drive device comprises a linkage 32 translating a unidirectional rotary motion of around more than 360° into an oscillating translation of the scanning device 20 along the path. The linkage 32 comprises a driven gear 34 and a driving gear 36 as well as two levers 38 and 40 linked through a bar 42.

The transfer device 4 comprises also control means 50 adapted to generate a three dimensional model of the crop heap surface in the receptacle and/or the receptacle based on the information generated by the scanning device 12. The control means 50 is also adapted to control the drive device 30 in order to drive the scanning device 12 along the path 20.

The crop transfer device is used in the following manner.

Crop is conveyed via the conveyor 8 and the crop is discharged through the conveyor outlet 10. The surface of a heap in the receptacle created by the discharged crop and or the receptacle is scanned by the scanning device 12. The conveyor 8 is moved with respect to the receptacle as a function of the information generated by the scanning device 12. In particular the control means 50 controls a displacement of the conveyor based on the information generated by the scanning device.

What is claimed is:

1. A crop transfer device for transferring crop to a receptacle, the device comprising:
    a conveyor for transferring the crop, the conveyor defining a conveyor plane (CP), the conveyor having a conveyor outlet defining an outlet direction (OD) which is the direction of the crop falling from the conveyor at the conveyor outlet;
    a scanning device adapted to scan the surface of crop situated below the conveyor outlet; and
    a mounting device by which the scanning device is mounted to the conveyor with a translational mobility of the scanning device with respect to the conveyor along a path.

2. The crop transfer device according to claim 1, wherein the mounting device comprises a mounting arm rotationally linked to the conveyor around a mounting axis of rotation (x-x), and wherein the scanning device is attached to the mounting arm at a distance to the mounting axis of rotation.

3. The crop transfer device according to claim 2, wherein the scanning device is attached to the mounting arm at a distance to the mounting axis of rotation so that the path has an arc shape.

4. The crop transfer device according to claim 2, wherein the mounting device comprises drive means for driving the scanning device along the path and wherein the drive device comprises a linkage translating a unidirectional rotary motion of around more than 360° into an oscillating translation of the scanning device along the path.

5. The crop transfer device according to claim 1, wherein the scanning device is arranged above the conveyor plane with respect to the outlet direction.

6. The crop transfer device according to claim 1, wherein the conveyor comprises an outlet wall, and wherein the path of the scanning device is situated outside of the outlet wall, which is a side of the wall opposite the conveyor outlet.

7. The crop transfer device according to claim 6, wherein the outlet wall extends perpendicular to the conveyor plane.

8. The crop transfer device according to claim 6, wherein, the path is situated completely on the outside of the outlet wall.

9. The crop transfer device according to claim 1, wherein the scanning device comprises a scan head adapted to scan in a scan plane (SP).

10. The crop transfer device according to claim 9, wherein the scan head comprises a 2D-Laserscanner.

11. The crop transfer device according to claim 9, wherein the scan head is a rotational scan head having a rotational mobility around a scan axis (A-A).

12. The crop transfer device according to claim 1, wherein the mounting device comprises drive means for driving the scanning device along the path.

13. The crop transfer device according to claim 1, wherein the crop transfer device comprises control means adapted to generate a three-dimensional model of the crop heap surface and the receptacle based on the information generated by the scanning device.

14. The crop transfer device according to claim 1, wherein the crop transfer device comprises control means adapted to generate a three-dimensional model of the crop heap surface or the receptacle based on the information generated by the scanning device.

15. The crop transfer device according to claim 1, wherein the crop transfer device is a device for transferring root crop.

16. A method of transferring crop into a receptacle using a crop transfer device according to claim 1, the method comprising:
conveying crop via the conveyor;
discharging the conveyed crop through the conveyor outlet;
scanning the surface of a heap in the receptacle created by the discharged crop and/or the receptacle by the scanning device; and
moving the conveyor with respect to the receptacle as a function of the information generated by the scanning device.

17. The crop transfer device according to claim 1, wherein the conveyor plane (CP) is coplanar with an upperside of a conveyor belt.

18. The crop transfer device according to claim 1, wherein the mounting axis of rotation (x-x) is perpendicular to the conveyor plane (CP).

* * * * *